United States Patent [19]

Grundei et al.

[11] Patent Number: 5,507,827
[45] Date of Patent: Apr. 16, 1996

[54] PELVIS PART ENDOPROSTHESIS

[75] Inventors: Hans Grundei; Reiner Gradinger, both of Lübeck, Germany

[73] Assignee: Eska Medical GmbH & Co., Germany

[21] Appl. No.: 254,333

[22] Filed: Jun. 6, 1994

[30] Foreign Application Priority Data

Jun. 8, 1993 [DE] Germany .................. 43 19 010.3

[51] Int. Cl.⁶ .................. A61F 2/32; A61F 2/34
[52] U.S. Cl. .................. 623/22; 623/18; 623/23
[58] Field of Search .................. 623/22, 19, 23, 623/18

[56] References Cited

U.S. PATENT DOCUMENTS

| | | | |
|---|---|---|---|
| 4,828,565 | 5/1989 | Duthoit et al. | 623/22 |
| 4,883,489 | 11/1989 | Grundei et al. | 623/22 |
| 5,021,062 | 6/1991 | Adrey et al. | 623/22 |
| 5,176,711 | 1/1993 | Grimes | 623/22 |
| 5,326,368 | 7/1994 | Collazo | 623/22 |
| 5,344,458 | 9/1994 | Bonutti | 623/19 |

FOREIGN PATENT DOCUMENTS

| | | | |
|---|---|---|---|
| 0501207 | 9/1992 | European Pat. Off. | 623/22 |
| 2614781 | 11/1988 | France | 623/22 |
| 2660546 | 10/1991 | France | 623/22 |
| 2605180 | 8/1977 | Germany . | |
| 3629799 | 3/1988 | Germany . | |
| 3710233 | 10/1988 | Germany . | |
| 9111221 | 10/1991 | Germany . | |
| 4133433 | 5/1993 | Germany . | |
| 2016275 | 9/1979 | United Kingdom . | |

*Primary Examiner*—David H. Willse
*Assistant Examiner*—Bruce E. Snow
*Attorney, Agent, or Firm*—Panitch Schwarze Jacobs & Nadel

[57] ABSTRACT

A pelvis part endoprosthesis for the replacement of a pelvis part in the region of the hip joint includes a main body (100) that has a hemispherical recess (101) for seating of an artificial hip joint socket, as well as a projecting neck (102) in which at least one locating hole (103, 104) is formed. The longitudinal axis of this hole forms with the polar axis (105) of the recess (101) an angle which lies in the range between 20° and 30°. The endoprosthesis further includes a first connecting element (200), by means of which a connection of the main body (100) with the ilium region (400) of the remaining pelvis is realized. The connection is produced by means of a self-locking seating of a peg (201) of the first connecting element (200) in at least one locating hole (103, 104). The peg (201), when viewed from the dorsal towards the ventral direction, is inclined at an angle in the range between 25° and 45°, and is laterally inclined from the medial at an angle between 0° and 10°. The endoprosthesis has the possibility of being individually created from a set, with the individual elements being exchangeable even during an operation, and the installed position being adjustable even during the implantation.

16 Claims, 7 Drawing Sheets

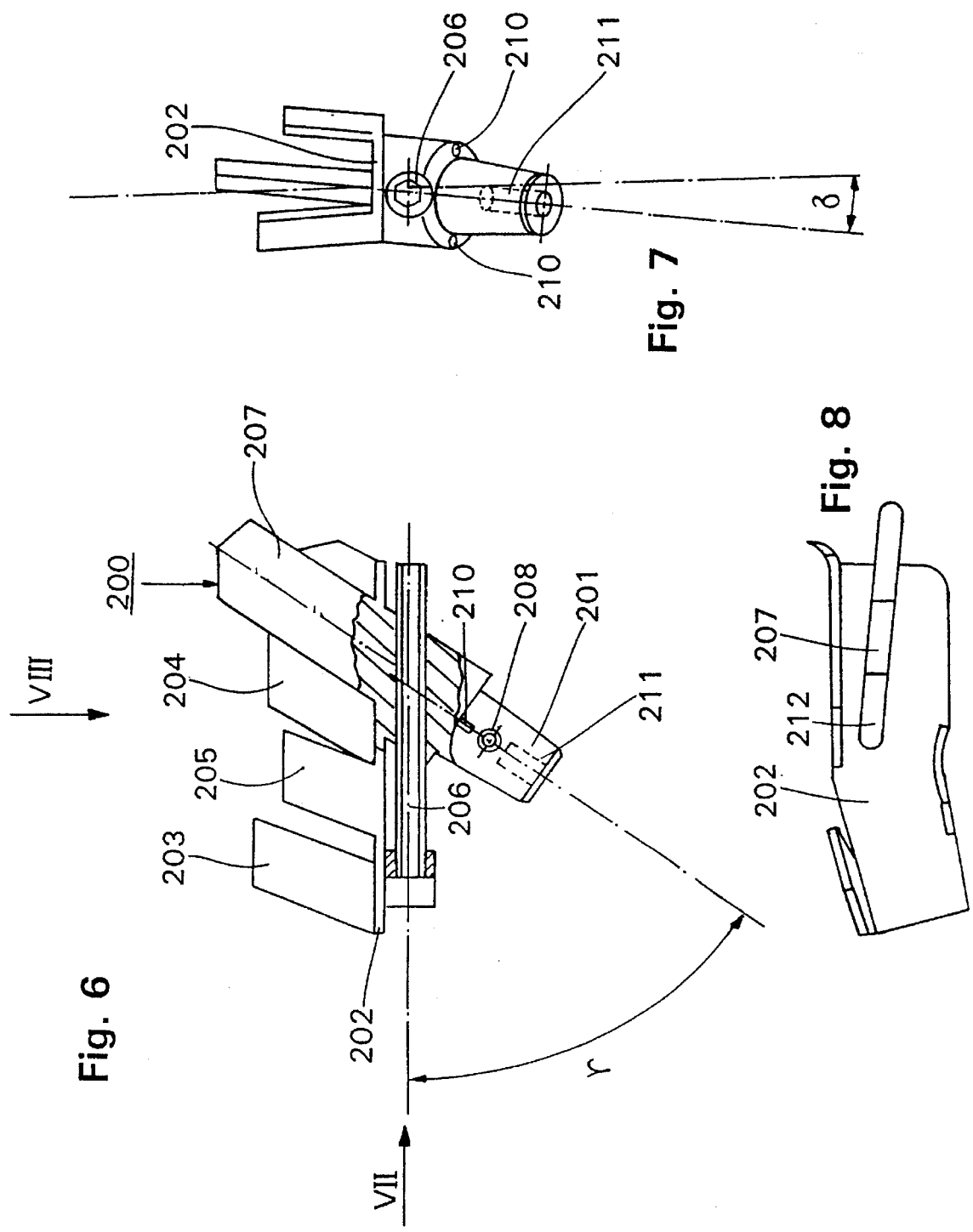

PELVIS PART ENDOPROSTHESIS

FIELD OF THE INVENTION

The invention relates to a pelvis part endoprosthesis for the replacement of a pelvis part in the region of the hip joint, with a main body that has a dome-shaped recess for the seating of an artificial hip joint socket, and a first connecting element for producing a connection of the main body with the ilium region of the remaining pelvis.

BACKGROUND OF THE INVENTION

An endoprosthesis with these features as sub-features is known from DE 36 29 799 A1. Described therein are two connecting elements joined by means of pegs with corresponding receiving seats on the main body, whereby one of the connecting elements—as mentioned—is used for producing a connection of the main body with the ilium region of the remaining pelvis, while the other connecting element serves for joining the main body with the pubic bone region of the remaining pelvis. The actual fixing of the connecting elements to the remaining bone is carried out by means of plate parts that are brought into position against the bone parts and that have holes through which bone screws are screwed transversely through the remaining bone.

Admittedly, newer diagnostic procedures permit the detection of tumors by means of computer tomography and the simulation in plastic of the bone regions as well as the regions stricken by the tumor. With the help of these models, surgeons can then determine before the actual operation how the implant ultimately must look, which resections must be carried out ahead of time, and how the individual procedures must be done during the operation. These preparatory measures are indeed very helpful, but do not guarantee a smooth operative procedure. It is felt to be particularly disadvantageous in the case of the known endoprosthesis that it is too inflexible.

Thus, during massive operations, in the course of which parts of the entire pelvis, including the natural joint socket, are resected, it can very easily happen that the bone screws are screwed into the bones at places that are at first thought to be correct, whereas it can turn out after the assembly of the modular prosthesis that a positioning correction is urgently needed. In this case, the bone screws must then be at least partly removed, one or the other of the connecting elements must be placed into a different position, and the bone screws screwed back into the bones that are in any case weakened by the resection, while leaving behind through the bones holes from the first attempt which are now no longer necessary.

In addition to that, a swivelling of the main body around the one peg of the first connecting element is certainly possible before the so-called fixed site between the first connecting element and the main body has been established. In any event, if in the case of the known endoprosthesis the main body swivels around the axis of the peg, then the main body is rotated out of the anatomically determined plane of a natural hip joint socket, so that in some cases it is possible for the artificial hip joint to come to rest at a different height than the natural hip joint which is left in the patient's body on the other side of the pelvis. The consequences of this are possible excessive loads on the remaining bone, from which significant postoperative complications can result.

An additional endoprosthesis for the replacement of a human pelvis part has become known from DE-41 33 433 C1. In comparison with the endoprosthesis from the above-mentioned reference, the endoprosthesis described in this document has a greater degree of freedom in its adjustability. It consists of an outer shell, whose wall is penetrated by a large number of holes bored through it. A screw is set through one of these bored holes in order to be screwed together with a conical peg that is formed on a connecting element for the ilium stump. An intermediate piece between the peg and the outer shell acts as a spacer. The selection of the hole through which the screw is placed is to be made by the surgeon during the operation, so that a replacement positioning of the outer shell in relation to the remaining pelvis parts can be made. Thereafter, the outer shell is joined with the ilium stump by means of additional connecting pieces.

Quite apart from the fact that the metal outer shell is significantly weakened mechanically by the large number of holes bored through it, it also has to be considered disadvantageous that the surgeon must concern himself with a large number of small parts during the operation, until the endoprosthesis attains a replacement positioning. This large number of elements must be reset with every change of the installed position.

SUMMARY OF THE INVENTION

Against this highlighted background, it is an object of the present invention to provide a pelvis part endoprosthesis that can be constructed from a set of elements in which the individual elements can be exchanged even during the operation and whose installed position can be adjusted during the operation with no difficulty.

The pelvis part endoprosthesis in accordance with the invention is constructed from at least two parts or elements from the set, namely from a main body that has a hemispherical recess for seating of an artificial hip joint socket and a projecting neck in which is formed at least one locating hole whose longitudinal axis forms with the polar axis of the recess an angle $\beta$ in the range of $20°<\beta<30°$, preferably $\beta=25°$, as well as from a first connecting element for producing a connection of the main body just described with the ilium region of the remaining pelvis, whereby the connection is produced by means of a self-locking seating of a peg of the first connecting element in the locating hole in the projecting neck of the main body. The peg, when viewed from the dorsal toward the ventral direction, is inclined at an angle $\gamma$ in the range $25°<\gamma<45°$, preferably $\gamma=35°$, and is inclined laterally from the medial at an angle $\delta$ in the range $0<\delta<10°$, preferably $\delta=5°$. If so desired, the above-described peg can be provided with rotation-prevention pins that engage in corresponding bores in the projecting neck of the main body. An additional securing screw can be provided in order to make the seating of the peg in the locating hole permanent and immovable.

The specification of the above-mentioned angle ranges is based on the following findings: Of course, the absolute dimensions of a pelvis vary from patient to patient. Surprisingly, however, what does not vary over a wide range are the relative dimensions and relative positions (angles). This means, therefore, that the same angles are found again and again between, for example, the pubic bone and the ilium in pelvises of the most widely varying sizes. This discovery makes it possible to manufacture a pelvis part endoprosthesis such as the one described in accordance with standardized data.

The minimum implant is thus comprised of two elements, the main element and a connecting element to the ilium stump. Beyond that, however, the set for the production of endoprostheses makes it possible to produce additional embodiments of the endoprosthesis, which will be described in more detail in the following.

In accordance with an advantageous further development, the projecting neck of the main body has not just one, but two locating holes. Their angular relationship is such that their longitudinal axes form an angle $\alpha$ in the range $40°<\alpha<\alpha°$, preferably $=50°$, with each other, and each of which forms an angle $\beta$ in the range of $20°<\beta<+°$, preferably $\beta=25°$, with the polar axis of the recess.

This configuration makes it possible, for one thing, for the main body to be used both for the right side of the pelvis as well as for the left side, without limiting the options for adjustment during the operation. In addition, the configuration with two locating holes also makes it possible to connect an additional connecting element, as is described in the following.

In accordance with an additional advantageous embodiment, to the minimum implant that is comprised of the main body with two locating holes and the first connecting element, a second connecting element is provided for producing a connection of the main body with the pubic bone region of the remaining pelvis. The connection can be produced by means of a self-locking seating of a peg-shaped connecting member in one of the locating holes in the projecting neck of the main body.

It is preferable that the two locating holes have the same size and the same shape, and that the external contours of the peg-shaped connecting member of the second connecting element correspond to those of the peg of the first connecting element. This further development makes possible the use of the main body in either the right or the left region of the pelvis, as well as the ability to likewise use the second connecting element on either the right or on the left.

It is advantageous that the locating holes are configured as conical split taper sockets, and that the peg and the peg-shaped connecting member are configured as conical plug-in pegs.

It is also advantageous that the locating hole or the locating holes in the projecting neck reach all the way into the inner dome of the main body. In this way, the locating holes are accessible from the interior of the main body as well, in order to be able to undertake, for example, the screwing in of the peg-shaped member of the second connecting element and/or the peg of the first connecting element.

The above-described further developments relate to the main body. However, advantageous further developments of both the first and the second connecting elements as well are described in the following.

In accordance with a first embodiment, the first connecting element has a base for placement against the ilium region. The ilium region after the resection consists of the ilium stump. By means of a specialized grinding template, normalized and standardized resections can be performed. From the base, two bracket vanes project laterally and one bracket vane projects medially; the ilium stump comes to rest between them. A rod is provided that can travel along and penetrate through the base. The rod is to be set in a channel that is to be drilled intramedullarly in the remaining pelvis. The peg that is to be inserted in one of the locating holes in the main body is formed on the rod end in the direction towards the main body.

Operatively, then, following the resection of the ilium region, the surgeon proceeds in such a way that an intramedullary channel is cut into the ilium bone into which the above-mentioned rod is to be inserted. A characteristic feature is that this rod can travel along the base of the connecting element by means of a mechanical adjusting device. This adjusting device can, for example, take the form of a mechanism with a threaded spindle. The rod penetrates the base, since the base is provided with an oblong hole. This ability to travel offers a sufficient degree of freedom for adjustment of the endoprosthesis during the operation.

It is preferable that the rod be arranged offset in the dorsal direction by 5 to 20 mm from the axis of the peg at the height of the first connecting element. This is provided in view of the fact that an intramedullary channel can then be made in the ilium stump at a location where sufficient spongiosa in the bone can be removed by grinding and sufficient space can be created so that the rod can be essentially intramedullarly inserted.

If a second connecting element is also provided for the connection of the main body with the pubic bone stump for the construction of the implant, two different embodiments are provided for this case.

Both embodiments have in common that the second connecting element has on the pubic bone side a connecting piece with a flange that can be secured to the pubic bone stump, a ball cage, and a bridging element whose one end is configured as a ball that is carried in the ball cage, and whose other end can be joined with the peg-shaped connecting member.

Both embodiments of the second connecting element also have in common that the respective bridging element penetrates through one of the respective grooves in the projecting neck of a locating hole in the main body and into the peg-shaped connecting member, and is screwed together with it at that point.

The first embodiment of the bridging element comprises a threaded sleeve which carries at the end that is toward the main body another ball that engages with a ball cage that has secured on its back side a fixing bar that can be screwed together with the peg-shaped connecting member. Visually speaking, then, this bridging element has a shape that is approximately that of a dumbbell.

In the case of the second embodiment of the second connecting element, the bridging element comprises a wire rope that can be screwed into the interior of the peg-shaped connecting member.

The first-mentioned dumbbell-shaped bridging element serves to make a more solid connection between the main body and the pubic bone stump. The bridging element in the form of a wire rope is somewhat softer. It can transmit only tension forces which are, however, the ones that overwhelmingly prevail; that is, compression forces on the wire rope are practically non-existent.

All of the balls of the bridging elements are retained in a sort of ball cage that preferably comprises a bearing shell made, for example, of high density polyethylene or other suitable sliding partners. In this way, abrasion of metal can be avoided.

The special configuration of the bridging elements serves to allow micro movements of the endoprosthesis in relation to the remaining pelvis. In the case, for example, of the endoprosthesis in accordance with the above-mentioned DE 36 29 799 C2, the implant there is completely rigid and bridges the ilium and the pubic bone. As a result of the completely different moduli of elasticity of the metal of the endoprosthesis on the one hand, and the bone remaining in the body on the other, this bone will be over-stressed due to the rigid transfer of forces on the part of the implant. This should be avoided by the configuration in accordance with the present invention.

BRIEF DESCRIPTION OF THE DRAWINGS

The foregoing summary, as well as the following detailed description of preferred embodiments of the invention, will be better understood when read in conjunction with the appended drawings which show further features and advantages of the invention. For the purpose of illustrating the invention, there are shown in the drawings embodiments which are presently preferred. It should be understood, however, that the invention is not limited to the precise arrangements and instrumentalities shown. In the drawings:

FIG. 6 shows a side view of one embodiment of the first connecting element;

FIG. 7 shows the first connecting element taken in the direction of the arrow VII in FIG. 6;

FIG. 8 shows the first connecting element taken in the direction of the arrow VIII in FIG. 6;

In the drawing figures, the same parts are represented by the same reference numbers throughout.

DETAILED DESCRIPTION OF PREFERRED EMBODIMENT

Figure 1:
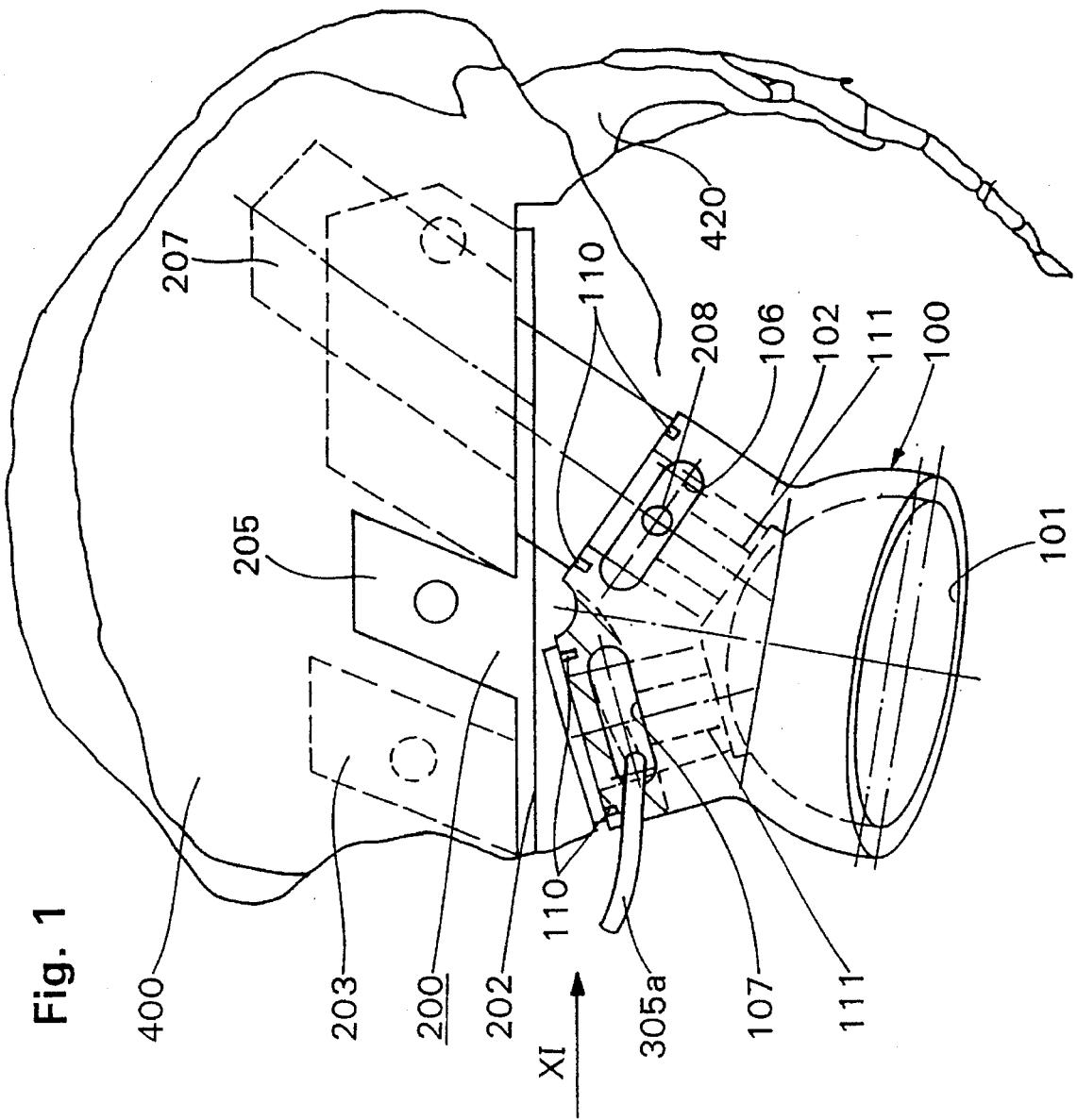
FIG. 1 shows a left pelvis part endoprosthesis comprising a main body and a first connecting element in the implanted state at the ilium stump.

FIG. 1 provides a first overview. It shows a remaining pelvis with the ilium stump 400 and the sacrum 420. Secured to the ilium stump is the first connecting element 200, which frames the ilium stump with its bracketing vanes 203, 205. Rod 207 engages intramedullarly with a channel that has been drilled in the ilium stump 400. The rod penetrates the base of the first connecting element 200 in a manner that is described in more detail further below. On the other side of the base, formed on the rod 207 is a peg 201 (see FIG. 6) which serves as a joining element to the main body 100 of the endoprosthesis. The peg is—as can readily be seen in FIG. 1—inclined from the dorsal towards the ventral direction in a range of angles of from 25° to 45°. This is discussed in more detail further below.

Figure 2:
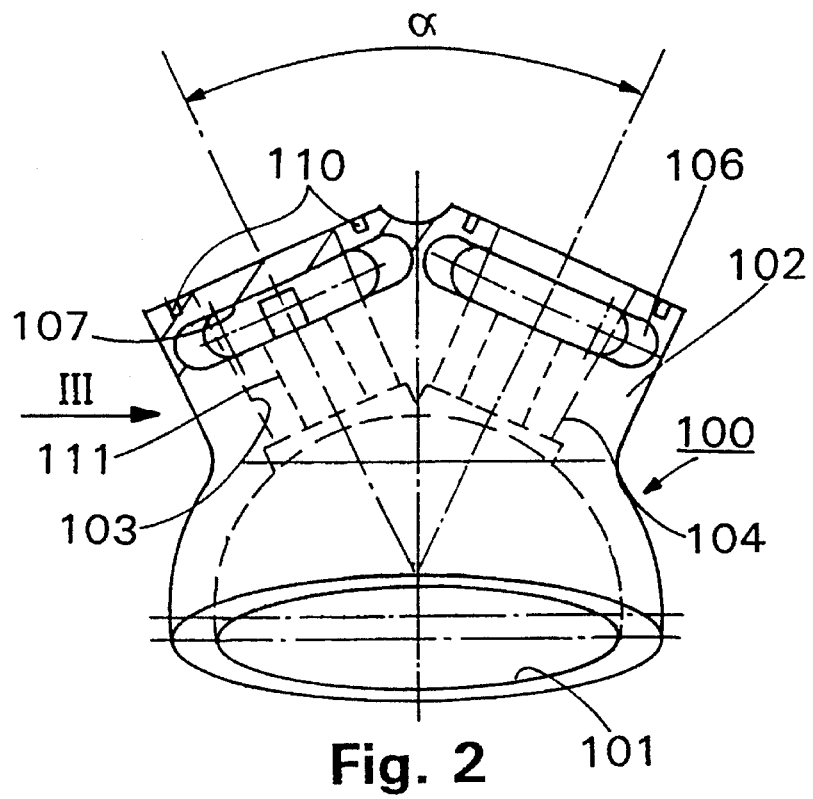
FIG. 2 shows a side view of one embodiment for the main body.

The illustrated main body 100 has available a hemispherical-shaped recess 101, which serves for seating of an artificial hip joint socket. The main body has a projecting neck 102 in which, in the embodiment shown, two locating holes 103 and 104 are formed. The left (as seen in FIGS. 1 and 2) region of the projecting neck 102 is provided with suggested dotted lines in order to make clear the way a different embodiment looks, in which the left locating hole does not need to be present.

In the present case, however, a bridging element 305a of an embodiment of a second connecting element engages with the left locating hole.

Also shown are bores 110 in the periphery of the locating hole walls; these bores are provided as security against rotation. Securing pins that are correspondingly arranged on the peg of the first connecting element engage with these bores. This represents an additional safeguard against rotation. Externally on the projecting neck 102 of the main body, on both sides of both locating holes, there are provided, two grooves 106, 107 that run tangentially and that breach the locating holes tangentially in some regions. The purpose of these grooves is to allow the bridging element 305a to pass through the locating hole wall to a peg-shaped connecting member of a second connecting element.

In the case of the first connecting element 200, there is provided in the projecting region of the peg a securing pin 208 that is pressed into the groove 106 by means of spring pressure upon production of the self-locking seating of the peg in the locating hole.

Figure 3:
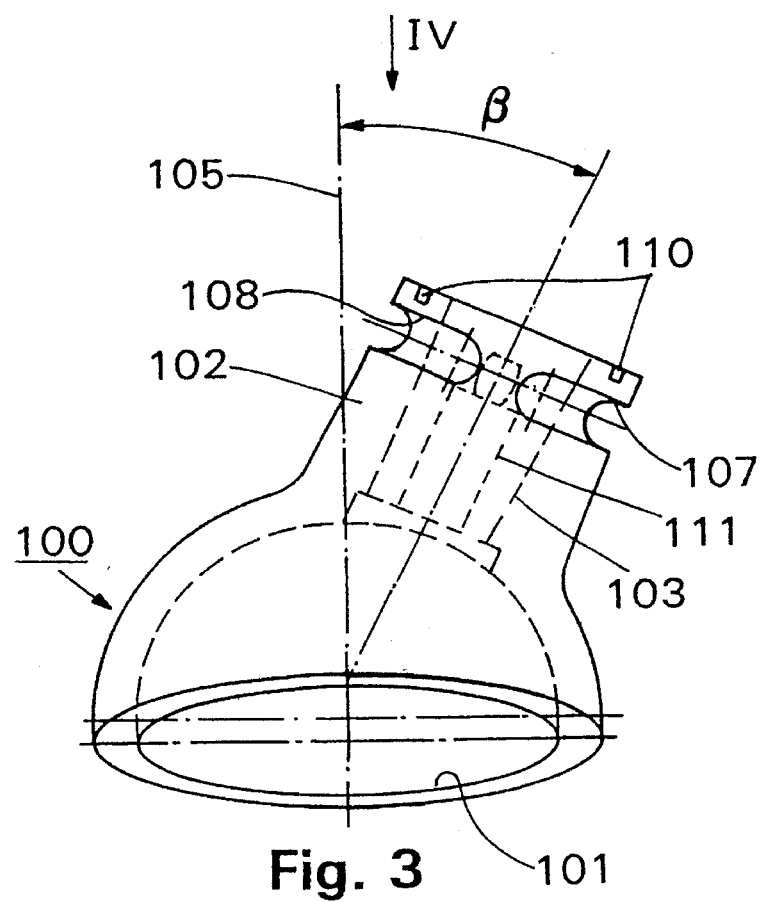
FIG. 3 shows a view of the main body taken in the direction of arrow III in FIG. 2.

FIG. 2 shows the main body 100 with the projecting neck 102 with two locating holes. The locating holes are so arranged that they form between them an angle $\propto$, which lies in the range between 40° and 60°, and preferably amounts to 50°. In conjunction with FIG. 3, it becomes clear that the longitudinal axes of both holes make an angle $\beta$ with the polar axis 105, which lies in the range between 20° and 30°, and preferably amounts to 25°. FIG. 3 also applies for the case in which only one locating hole is provided in the projecting neck 102.

Figure 4:
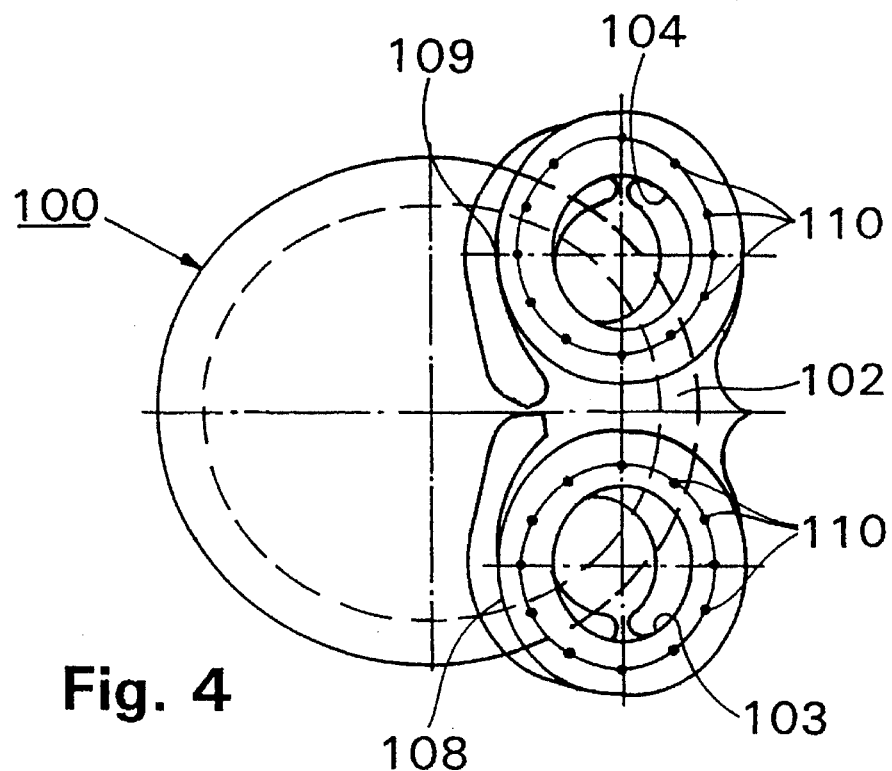
FIG. 4 shows a view of the main body taken in the direction of arrow IV in FIG. 3.

Also indicated in FIGS. 2 and 3 is screw thread 111 in the peg of a connecting element, into which a screw can be screwed as an additional safeguard against a loosening of the self-locking connection. Also made clear once again in FIGS. 2 through 4 is the two-sided arrangement of tangential grooves 106 through 109. In addition, in FIG. 4 the concentric arrangement of the securing bores 110 around the openings in the locating holes 103 and 104 is made particularly clear.

Figure 5:
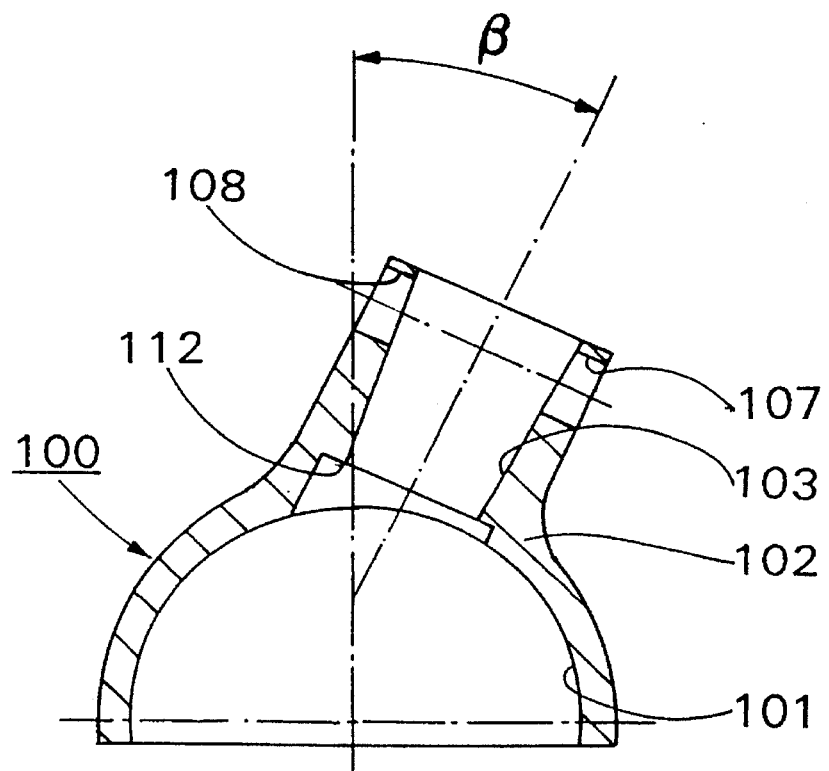
FIG. 5 shows a sectional view of the main body in generally the same direction as FIG. 3.

FIG. 5 shows a sectional view of the main body 100 with the elements that have already been described. In FIG. 5, however, it is made especially clear that the locating hole 103 reaches all the way into the inner dome 101 of the main body 100. In the interior region there is provided a ring shoulder 112, against which the head of a screw can lie when, for example, the peg 201 of the first connecting element 200 with an inner screw thread 211 is positioned in the locating hole 103, and the screw is screwed into the inner thread 211.

FIG. 6 shows a side view of one embodiment of the first connecting element 200, that is the element that produces the connection of the ilium stump 410 to the main body 100.

Connecting element 200 has a plate-shaped base 202, from which two bracketing vanes 203 and 204 project laterally and one bracketing vane 205 projects medially upward. The ilium stump comes to rest on the plate-shaped base 202, and is then bordered by the bracketing vanes 203, 204 and 205. In any case, the prerequisite for this is that an indentation has been ground into the spongy material of the remaining ilium, into which the rod 207 of the connecting element 200 can be placed. The first connecting element is thus anchored intramedullarly. An important secondary aspect in general, is the fact that on the outside and facing the ilium stump, the rod, as well as the plate-shaped base, can have a three-dimensional, open-mesh, spatial network structure made of metal, into which bone material can grow for the permanent fixing of the implant.

The rod goes through the base 202 in an oblong hole 212 (FIG. 8). Below the base 202, the rod 207 terminates as the peg 201.

It is fundamental that the peg 201 when viewed from the dorsal towards the ventral is inclined at an angle γ, whereby the angle γ lies in the range between 25° and 45°, and preferably amounts to 35° (FIG. 6). In addition, the peg is laterally inclined from the medial at an angle δ, which lies in the range from 0° to 10°, and preferably amounts to 5°(FIG. 7).

Also visible in FIG. 6 in addition is the securing pin 208, which—as is indicated in FIG. 1—springs under spring pressure into the tangential groove 106 after reaching the final position in the locating hole.

Visible as well are the rotation-preventing securing pins 210, which are arranged at the base of the peg and engage with the bores 110 in the main body 100 after forming the connection with the main body.

In addition, in the embodiment shown, the rod 207 is offset from the axis of the peg 201 by a few millimeters in the dorsal direction. This offset or displacement can amount to between 5 and 20 mm in the implementation. This offset arrangement is beneficial for anatomical reasons, since the rod 207 can then be placed in an intramedullary area that offers enough space to do this.

In the embodiment shown, there is in addition a mechanical adjusting device 206 in the form of a threaded spindle, with the help of which the rod can be moved back and forth in the oblong hole 212 in the base 202 until the optimum position has been determined in the course of the operation.

Figure 9:
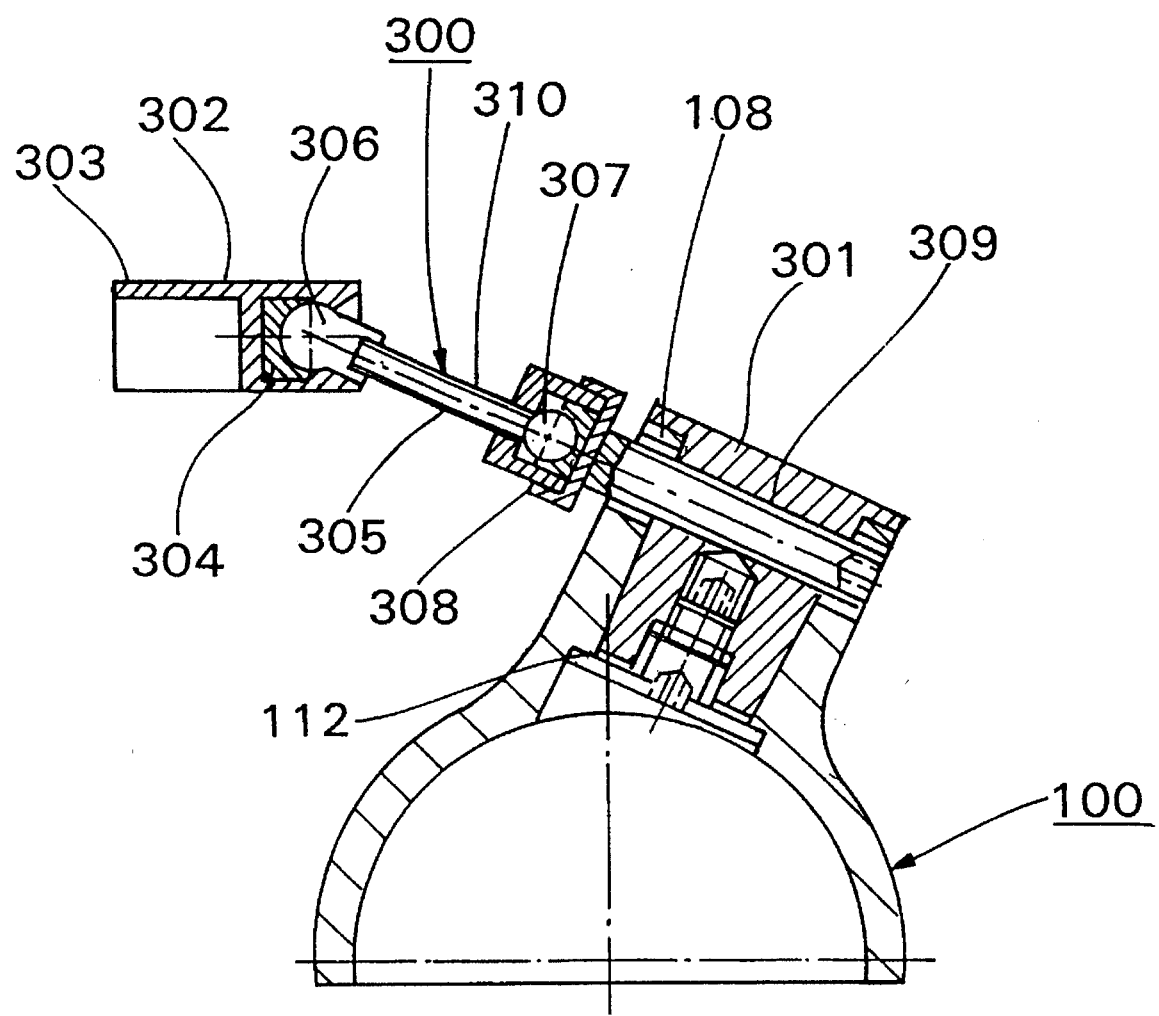
FIG. 9 shows a sectional view through the main body with a second connecting element mounted on it in accordance with one embodiment.

From FIG. 9 the connection between the main body 100 and the peg-shaped connecting member 301 can be seen. In the embodiment shown, this element—like the peg 201 of the first connecting element 200—is configured as a conical plug-in peg that can be inserted into the locating hole, which is correspondingly configured as a conical split taper socket. Shown in addition is the way in which a securing screw engages from the inside of the dome into the peg-shaped connecting member 301, whereby the screw head lies against the ring shoulder 112.

The essential feature of FIG. 9, however, is the second connecting element 300 for connection of the pubic bone stump 410 with the main body 100. The connecting piece 302 on the pubic bone side has a flange 303 that is to be secured to the pubic bone stump. The securing takes place, for example, by means of bone screws (not shown). Formed onto this flange is a ball cage 304 in which a ball 306 of the bridging element 305 is carried. The bridging element in the embodiment shown comprises a threaded sleeve 310 that is adjustable in length and that bears at its other end an additional ball 307 that is carried in an additional ball cage 308 that has secured on its back side a fixing bar 309 that is screwed together with the peg-shaped connecting member 301. The fixing bar 309 also goes through the tangential groove 108, as has already been mentioned above.

This embodiment, which was described above as dumbbell-shaped, for the bridging element provides for a relatively secure connection between the pubic bone stump and the main body 100. This ball seating arrangement does, however, permit micro movements to be executed with respect to one another.

Figure 10:
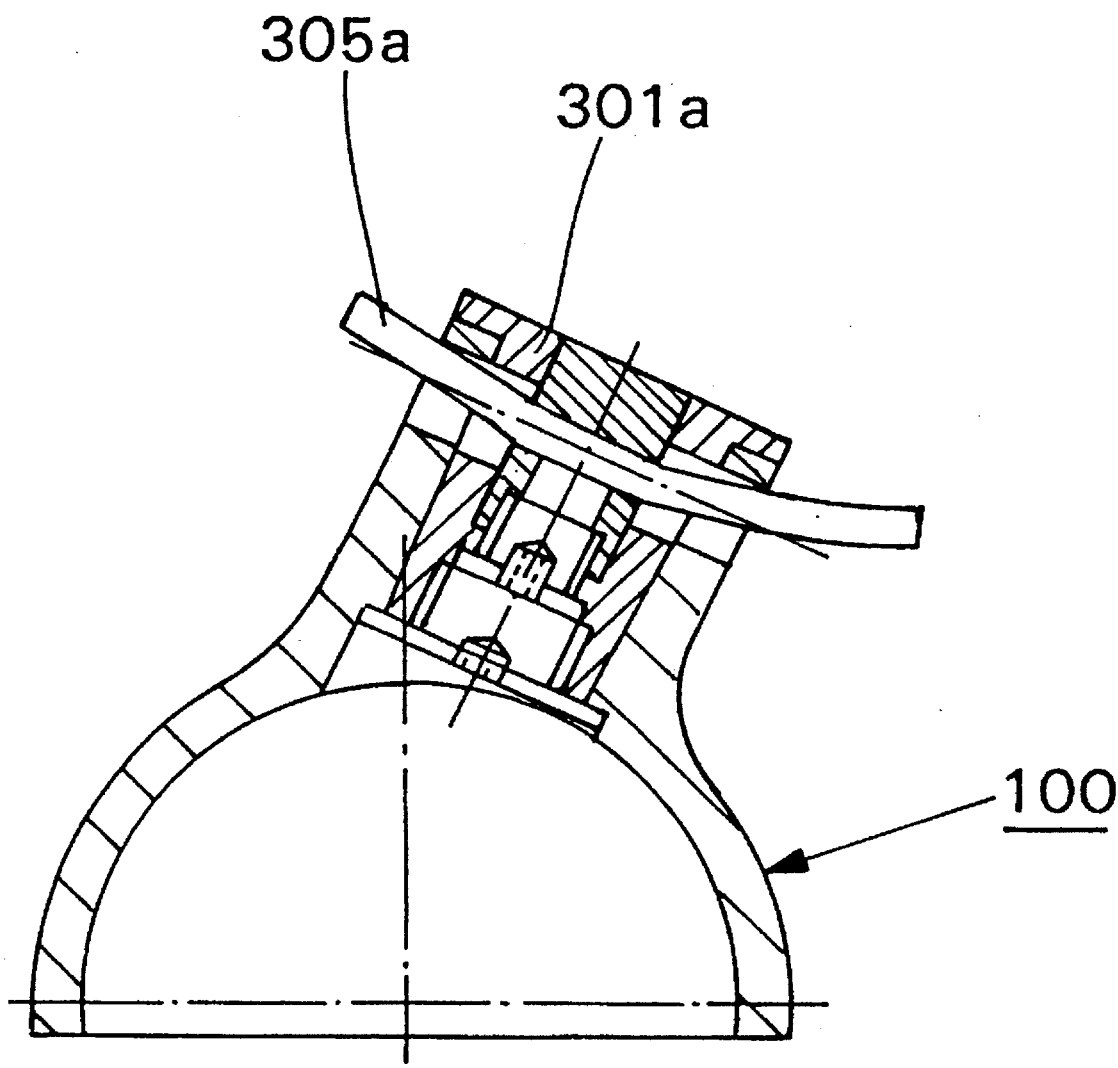
FIG. 10 shows a sectional view of the main body with a bridging element of a second connecting element in accordance with another embodiment.

A somewhat looser connection between the pubic bone stump and the main body is offered by another embodiment of the second connecting element, which does, however, make use of the parts 302, 303, 304 and 306 of the first embodiment. In any case, here there is no threaded spindle 305 with an additional ball cage 308 provided, but instead, a wire rope 305*a* (FIG. 10), which engages with a different peg-shaped connecting member 301*a* and is tensioned there. This tensioning can be pictured as the securing of a Bowden line.

Figure 11:
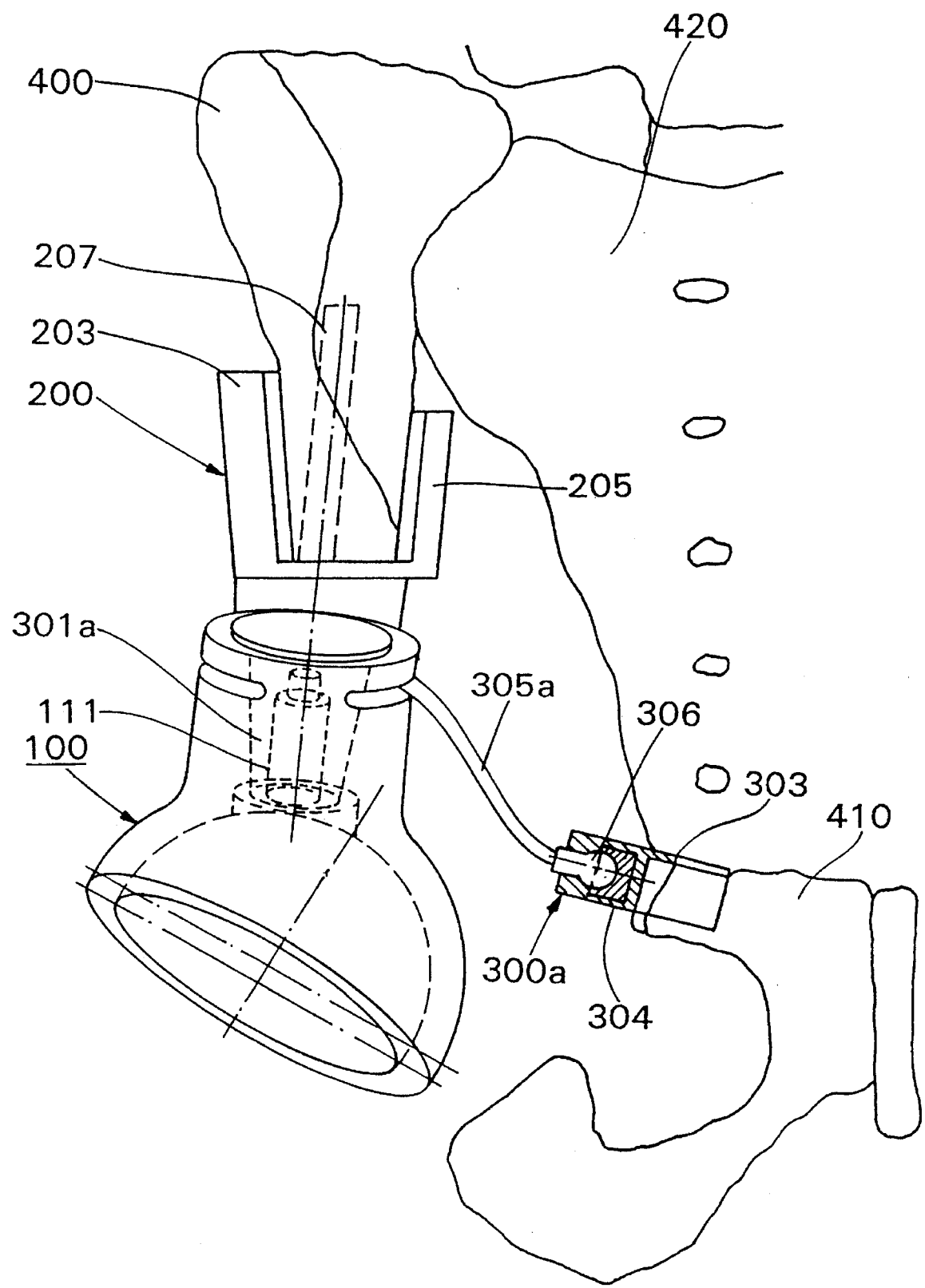
FIG. 11 shows a right pelvis part endoprosthesis with main body and two connecting elements taken ventrally.

In FIG. 11 a complete, three-part endoprosthesis can be seen that is equipped with the second embodiment of the second connecting element 300*a*. In conjunction with this, FIG. 11 shows a ventral (front) view of the right side pelvic endoprosthesis in the direction of the arrow XI in FIG. 1, but augmented by the second connecting element 300*a*.

The endoprosthesis according to the present invention is distinguished by the possibility that the individual elements can be exchanged even during the operation. Its installed position can also be adjusted with sufficient accuracy even during the implantation. Depending on the needs of the individual patient, it can be created from a set, without it being necessary for individual casting forms to be created for each patient, in order to be able to cast an individual implant in metal.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A pelvis part endoprosthesis for replacement of a pelvis part in a region of a hip joint, comprising a main body (100) having a hemispherical recess (101) for the seating of an artificial hip joint socket and a neck (102) projecting therefrom in which at least one locating hole 103, 104) is formed, a first connecting element (200) for connecting the main body (100) with an ilium region (400) of a remaining pelvis, said first connecting element (200) having a base (202) and a rod (207) configured for insertion into a channel to be formed intramedullarly in the remaining pelvis which terminates in a peg (201) adapted for self-locking seating in one of said locating holes (103, 104), the locating hole (103, 104) having a longitudinal axis which forms with a polar axis (105) of the recess (101) an angle β in a range of $20° < \beta < 30°$, and the peg (201), when viewed from a dorsal towards ventral direction, being inclined at an angle γ in a range of $25° < \gamma < 45°$ with respect to the base (202), and inclined laterally from a medial at an angle δ in a range of $0° < \delta < 10°$, the rod (207) having a longitudinal axis approximately parallel to the peg (201).

2. A pelvis part endoprosthesis according to claim 1, wherein β equals about 25°, γ equals about 35° and δ equals about 5°.

3. A pelvis part endoprosthesis in accordance with claim 1, wherein the projecting neck (102) has two locating holes (103, 104) whose longitudinal axes form an angle ∝ in the range $40° < \alpha < 60°$ with each other, and each of which axes forms an angle β in the range of $20° < \beta < 30°$ with the polar axis (105) of the recess (101).

4. A pelvis part endoprosthesis according to claim 3, wherein ∝ equals about 50° and β equals about 25°.

5. A pelvis part endoprosthesis in accordance with claim 3, further comprising a second connecting element (300) for connecting the main body (100) with a pubic bone region (410) of the remaining pelvis, said second connecting element having a peg-shaped connecting member (301)

adapted for self-locking seating in the other locating hole (103, 104).

6. A pelvis part endoprosthesis in accordance with claim 5, wherein the two locating holes (103, 104) have the same size and the same shape, and the peg-shaped connecting member (301) of the second connecting element (300) has a profile which corresponds to a profile of the peg (201) of the first connecting element (200).

7. A pelvis part endoprosthesis in accordance with claim 5, wherein the locating holes (103, 104) are configured as conical split taper sockets, and the peg (201) and the peg-shaped connecting member (301) are configured as conical plug-in pegs.

8. A pelvis part endoprosthesis in accordance with claim 1, wherein the locating hole (103, 104) reaches all the way into an inner dome of the main body (100), so as to be accessible from an interior of the main body.

9. A pelvis part endoprosthesis in accordance with claim 1, wherein the first connecting element (200) further comprises two bracketing vanes (203, 204) projecting laterally from the base, and one bracketing vans (205) projecting medially from the base, whereby the base (202) is configured for placement against the ilium region (400), and an ilium bone stump can be received and seated between said vanes, and wherein the rod (207) is movable along the base (202) by means of a mechanical adjusting unit (206) and penetrating the base through an oblong hole (212), and said rod having on one end the peg (201) formed in the direction towards the main body (100).

10. A pelvis part endoprosthesis in accordance with claim 9, wherein the rod (207) of the first connecting element (200) is arranged at an offset in the dorsal direction by 5 to 20 mm from a longitudinal axis of the peg (201).

11. A pelvis part endoprosthesis in accordance with claim 3, further comprising externally on the projecting neck (102), on both sides of both locating holes (103, 104), two grooves (106, 107; 108, 109) that run tangentially and that breach the locating holes tangentially in some regions.

12. A pelvis part endoprosthesis in accordance with claim 11, wherein the self-locking seating of the peg (201) in one of the locating holes (102, 103) is additionally secured by means of a securing pin (208) on the peg (201), said pin (208) locking into a groove (106, 107; 108, 109) in the projecting neck (102).

13. A pelvis part endoprosthesis in accordance with claim 5, wherein the second connecting element (300) has on a side facing the pubic bone a connecting piece (302) with a flange (303) adapted for securing to a pubic bone stump, a ball cage (304), and a bridging element (305, 305a), whose one end is configured as a ball (306) that is carried in the ball cage (304), and whose other end is adapted for connection with the peg-shaped connecting member (301, 301a).

14. A pelvis part endoprosthesis in accordance with claim 13, wherein the bridging element (305, 305a) penetrates into the peg-shaped connecting member (301, 301a) through a tangential groove (106, 107; 108, 109) in a locating hole (103, 104), and is screwed together with the member at that point.

15. A pelvis part endoprosthesis in accordance with claim 13, wherein the bridging element (305) comprises a threaded sleeve (310) having at an end toward the main body (100) an additional ball (307) that engages with a further ball cage (308) that has secured on its back side a fixing bar (309) adapted to be screwed together with the peg-shaped connecting member (301).

16. A pelvis part endoprosthesis in accordance with claim 13, wherein the bridging element (305a) comprises a wire rope adapted to be screwed into an interior of the peg-shaped connecting member (301a).

* * * * *